United States Patent
Eastwood et al.

(10) Patent No.: US 6,861,395 B2
(45) Date of Patent: Mar. 1, 2005

(54) METHOD AND COMPOSITIONS FOR INHIBITING THE GROWTH OF MICROORGANISMS IN METAL WORKING FLUIDS

(75) Inventors: Ian Michael Eastwood, Blackley (GB); Paula Louise McGeechan, Blackley (GB)

(73) Assignee: Arch UK Biocides Limited, West Yorkshire (GB)

(*) Notice: Subject to any disclaimer, the term of this patent is extended or adjusted under 35 U.S.C. 154(b) by 0 days.

(21) Appl. No.: 10/296,510

(22) PCT Filed: May 18, 2001

(86) PCT No.: PCT/GB01/02203

§ 371 (c)(1),
(2), (4) Date: Apr. 4, 2003

(87) PCT Pub. No.: WO01/92444

PCT Pub. Date: Dec. 6, 2001

(65) Prior Publication Data

US 2003/0168626 A1 Sep. 11, 2003

(30) Foreign Application Priority Data

May 26, 2000 (GB) .............................. 0012786

(51) Int. Cl.$^7$ .................... C10M 135/36; C10M 133/40
(52) U.S. Cl. ................... 508/275; 508/244; 508/583; 72/42
(58) Field of Search ........................ 508/275

(56) References Cited

U.S. PATENT DOCUMENTS

| | | | | |
|---|---|---|---|---|
| 3,517,022 A | | 6/1970 | Miller et al. ................ 260/304 |
| 5,364,874 A | * | 11/1994 | Morpeth ...................... 514/373 |
| 5,462,589 A | | 10/1995 | Nicholas et al. .......... 106/18.33 |
| 5,684,025 A | * | 11/1997 | Tsao et al. ................... 514/373 |
| 6,005,032 A | | 12/1999 | Austin .......................... 524/82 |
| 6,133,300 A | * | 10/2000 | Smith et al. ................. 514/373 |
| 6,482,814 B1 | * | 11/2002 | Bath et al. ................... 514/184 |

FOREIGN PATENT DOCUMENTS

| | | |
|---|---|---|
| GB | 2 230 190 A | 10/1990 |
| WO | 93/06723 | 4/1993 |
| WO | 99/65315 | 12/1999 |

OTHER PUBLICATIONS

Patent Abstracts of Japan, 57156405, Sep. 27, 1982.

* cited by examiner

*Primary Examiner*—Ellen M. McAvoy
(74) *Attorney, Agent, or Firm*—Morgan Lewis & Bockius LLP

(57) ABSTRACT

The present invention relates to a method of inhibiting the growth of microorganisms in a metal working fluid comprising adding to the metal working fluid a benzisothiazolin-3-one of the Formula (1): wherein R is $C_{4-5}$-alkyl; $R^1$ is hydroxy, halogen (especially chlorine), $C_{1-4}$-alkyl or $C_{1-4}$-alkoxy; and n is from 0 to 4.

(1)

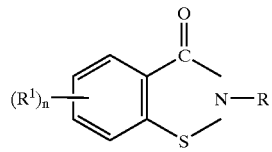

28 Claims, No Drawings

METHOD AND COMPOSITIONS FOR INHIBITING THE GROWTH OF MICROORGANISMS IN METAL WORKING FLUIDS

The present invention relates to a method for inhibiting the growth of micro-organisms in metal working fluids, especially soluble oil, synthetic and semi-synthetic metal working fluids, to metal working fluids treated according to the method and to compositions for use in the method.

Metal working fluids are used in metal processing operations such as cutting, drilling, tapping, grinding, milling, rolling, metal drawing, stamping and turning operations. The primary function of the metal working fluid is to provide cooling and lubrication to the metal and tools used in the processing operations. Metal working fluids are also used to protect metals and metal working tools against corrosion and rust formation, as temporary surface coatings to protect newly machined articles such as coils and springs, as quenching fluids and as casting fluids.

Metal working fluids can become contaminated with micro-organisms during preparation, storage and use of the fluid. Uncontrolled growth of micro-organisms in a metal working fluid can result in a number of undesirable problems, including loss of emulsion stability, pH changes, viscosity changes, loss of lubrication properties, discoloration, production of un-pleasant odours and the growth of slimes and other bio-mass deposits. The growth of slimes and other bio-mass deposits is particularly un-desirable because they can clog up the pipes, filters and screens used in metal working fluid handling systems.

To avoid these problems preservatives are added to metal working fluids to inhibit or prevent the growth of micro-organisms. Many preservatives are known for use in metal working fluids, U.S. Pat. No. 4,279,762 for example discloses the use of 3-isothiazolinones. Other commonly used isothiazolin-3-ones include 2-n-octyl-4-isothiazolin-3-one (commercially available from Rohm and Haas under the trademark Kathon 893 MW) and a mixture of 5-chloro-2-methyl-4-isothiazolin-3-one and 2-methyl-4-isothiazolin-3-one (commercially available from Rohm and Haas under the trademark Kathon MWC). Other commonly used preservatives include sodium pyridine-2-thiol-1-oxide (commercially available under the trademark Sodium Omadine from Arch Chemicals) and 3-iodo-2-propynyl-N-n-butyl carbamate (commercially available under the trademark Troysan polyphase from Troy Corporation).

Metal working fluids are often supplied to users as a concentrate which is diluted with water prior to use. The diluted concentrate can be used directly in metal processing operations. Alternatively the concentrate may be partially diluted and stored in holding vessels as a premix prior to further dilution and use in the metal processing operation. These concentrates and pre-mixes may be stored for long periods of time prior to use, often at an elevated temperature. It is therefore important that a preservative in a concentrate/pre-mix is able to withstand such hostile conditions without degrading and losing efficacy in the metal working fluid. If loss of the preservative occurs during storage micro-organisms can proliferate in the concentrate or pre-mix. Furthermore, when the concentrate/pre-mix is diluted prior to use further micro-biological degradation is possible because dilution may reduce the concentration of the preservative to a level below that required to inhibit growth of micro-organisms. If loss of preservative occurs further preservative must be added to the fluid which is both time consuming and expensive.

We have found that many of the preservatives commonly used in metal working fluids and concentrates, especially isothiazolinones and pyridinethiones, degrade and are lost during high temperature storage of the metal working fluids. There is therefore a need for a preservative which provides a high level of protection against the growth of undesirable micro-organisms and which is stable when stored in a metal working fluid under hostile temperature conditions.

GB 1,531,431 discloses 2-($C_{1-3}$-alkyl)-benzisothiazolin-3-ones and their use as industrial biocides, including fungicides, in aqueous systems such as metal working fluids, and paint films. The preferred compound is 2-methyl-benzisothiazolin-3-one because this is stated to have a higher activity than the compounds with longer chain alkyl groups.

EP 475,123 discloses 2-(n-$C_{6-8}$-alkyl)-benzisothiazolin-3-ones as industrial biocides and especially fungicides for paint and plastics materials.

We have now surprisingly found that certain benzisothiazolin-3-ones are stable to high temperature storage in metal working fluids and provide a high degree of protection against undesirable micro-biological growth.

According to a first aspect of the present invention there is provided a method for inhibiting the growth of micro-organisms in a metal working fluid comprising adding to the metal working fluid a benzisothiazolin-3-one of the Formula (1):

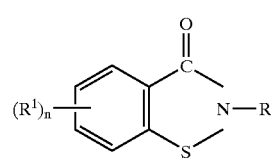

Formula (1)

wherein:

R is $C_{4-5}$-alkyl;

$R^1$ is hydroxy, halogen (especially chlorine), $C_{1-4}$-alkyl or $C_{1-4}$-alkoxy; and n is from 0 to 4.

R may be linear or branched but is preferably linear. Preferred groups represented by R include, for example n-pentyl, n-butyl, isobutyl and tert-butyl. It is especially preferred that R is n-butyl.

$R^1$, when present, is preferably located in the 5 and/or 6 position of the phenyl ring of the benzisothiazolin-3-one. However, it is particularly preferred that n is zero.

In view of the foregoing preferences, the preferred compound of Formula (1) is 2-n-butyl-1,2-benzisothiazolin-3-one. We have found that this compound is very stable to high temperature storage in metal working fluids. Furthermore this compound exhibits very good compatibility with a wide range of metal working fluids, particularly those which contain high levels of amines.

The compounds of the Formula (1) may be prepared by using known processes. A suitable process is described in GB 484,130 wherein a 2-chlorosulphenyl benzoyl chloride is reacted with an alkylamine.

Preferably the metal working fluid contains a microbiologically effective concentration of the compound of Formula (1). The concentration required to inhibit the growth of micro-organisms will depend upon the type of metal working fluid and the conditions under which it will be stored and used. We have found that a concentration of from 50 to 300, more preferably from 75 to 200 ppm and especially from 100 to 150 ppm by weight of the compound of Formula (1)

in the metal working fluid inhibits the growth of micro-organisms. However, in some applications it may be desirable to use a higher concentration, for example as a shock treatment to a fluid which has been heavily contaminated by fungal growth.

When the compound of Formula (1) is added to a concentrate or pre-mix it is preferred that a higher concentration of the compound of Formula (1) is used so that upon dilution the dilute fluid contains a sufficient concentration of the compound of Formula (1) to maintain protection against growth of micro-organisms during use of the metal working fluid. For example, if the concentrate/premix is diluted by 5 volumes of water prior to use in the metal processing operation it is preferred that the concentrate contains 5 times the above preferred concentrations of the compound of Formula (1).

The compounds of Formula (1) are suitable for use in a wide range of metal working fluid compositions, for example straight oils, quenching fluids, casting fluids and especially soluble oil, semi-synthetic or synthetic metal working fluids.

Metal working fluids are usually based upon formulations containing mineral oils, vegetable oils, animal derived oils or synthetic lubricants and derivatives and mixtures thereof. Suitable mineral oils include those derived from petroleum products, for example naphthenic and parrafinic based oils. Useful derivatives of mineral oils include sulphurised oils and chlorinated oils both of which exhibit good lubricity properties under extremes of pressure.

Straight oils are oil based products which are substantially free from water. Typically straight oils comprise mineral oils or a blend of mineral oils with fatty vegetable oils.

Soluble oils comprise an emulsion of mineral oil in water obtained by emulsifying the oil in water with a suitable emulsifying agent. The particle size of the oil in the emulsion is typically 2 to 10 µm. Soluble oils have a high mineral oil content of about 40 to 65% by weight oil.

Semi-synthetic metal working fluids are also mineral oil in water emulsions, however, these oils typically have an oil particle size of 0.1 to 1 µm and a lower oils content of about 5 to 40% by weight of oil compared to soluble oils.

Synthetic metal working fluids are based upon synthetic lubricants. Typically synthetic metal working fluids comprise an emulsion of one or more synthetic lubricant(s) in an aqueous medium. Suitable synthetic lubricants include glycols such as polyoxyalkylene glycols and glycol esters.

Quenching fluids generally comprise water and one or more humectants, for example glycols and glycol ethers.

Water-soluble corrosion products are formulations used to provide a short term corrosion protection to newly machined parts. These formulations typically contain synthetic lubricants similar to those found in synthetic metal working fluids and one or more corrosion inhibitors.

Casting fluids contain waxes, graphite, and other oil-based lubricants similar to those found in synthetic, semi-synthetic and soluble oil metal working fluids.

Preferably the metal working fluid has a pH of from 3 to 10 more preferably from 7 to 10 and especially from 6 to 9.

The metal working fluids may contain a number of other additives for example, emulsifying agents and surfactants which can be cationic or more preferably anionic or non-ionic; viscosity modifiers; defoaming agents; corrosion inhibitors; and oxidation inhibitors.

The present method is effective for inhibiting the growth of micro-organisms, especially fungi such as *Fusarium solani*, *Penicillium* sp., *Acremonium strictum* and *Geotrichum candidum*.

In a preferred embodiment the metal working fluid is a synthetic, semi-synthetic or soluble oil metal working fluid, because we have found that the compound of Formula (1) used in the present method provides particularly good protection against the growth of undesirable micro-organisms and exhibits excellent thermal stability in these fluids compared to conventional preservatives such as pyridinethione compounds, isothiazolin-3-ones and 3-iodo-2-propynyl-butylcarbamate.

The compound of Formula (1) may be added, to the metal working fluid directly. However, for ease of handling and dosing, it is generally convenient to formulate the compound of Formula (1) with a carrier.

The carrier may be a solid but is preferably a liquid medium and the formulation is preferably a solution, suspension, emulsion or micro-emulsion of the compound of Formula (1) in the liquid medium.

When the carrier is a liquid it is generally selected so that the formulation is compatible with the metal working fluid to be protected. For example, if the metal working fluid is a straight oil, i.e. essentially oil based, the carrier is preferably a solvent, especially a non-polar solvent such as white spirits. When the metal working fluid is an aqueous based formulation such as a synthetic, semi-synthetic or soluble oil, the carrier is preferably water or a water-miscible organic solvent or mixture thereof. Suitable water-miscible organic solvents include alcohols, preferably $C_{1-6}$-alkanols, for example methanol, ethanol, propanol and isopropanol; diols, preferably diols having from 2 to 12 carbon atoms, for example pentane-1,5-diol, ethylene glycol, propylene glycol, butylene glycol, pentylene glycol, hexylene glycol and thiodiglycol; oligo- and poly-alkyleneglycols, for example diethylene glycol, triethylene glycol, dipropylene glycol, polyethylene glycol (preferably with an average $M_n<1000$, more preferably $<500$) and polypropylene glycol (preferably with an average $M_n<1000$); triols, for example glycerol and 1,2,6-hexanetriol; mono-$C_{1-4}$-alkyl ethers of diols, preferably mono-$C_{1-4}$-alkyl ethers of diols having 2 to 12 carbon atoms, for example 2-methoxyethanol, 2-(2-methoxyethoxy)ethanol, 2-(2-ethoxyethoxy)-ethanol, 2-[2-(2-methoxyethoxy)ethoxy]ethanol, 2-[2-(2-ethoxyethoxy)-ethoxy]-ethanol and ethyleneglycol monoallylether; amides, for example N,N-dimethylformamide; cyclic amides, for example N-methyl-2-pyrrolidone, N-ethyl-2-pyrrolidone and 2-pyrrolidone; and sulphoxides, for example, dimethylsulphoxide. Especially preferred water miscible organic solvents are $C_{2-12}$-diols and polyalkylene glycols containing up to 12 carbon atoms, more especially ethylene glycol, propylene glycol, butylene glycol, diethylene glycol, triethylene glycol and dipropylene glycol. Diethylene glycol and dipropylene glycol are particularly preferred.

If the formulation is in the form of a suspension or emulsion, it preferably also contains a surface active agent to produce a stable dispersion or to maintain the non-continuous phase uniformly, distributed throughout the continuous phase. Any surface active agent which does not have a significant adverse effect on the biocidal activity of the compound of Formula (1) may be used. Suitable surface active agents include emulsifiers and surfactants and mixtures thereof. The emulsifiers/surfactants may by non-ionic, anionic or a mixture thereof. Suitable anionic emulsifiers and surfactants include alkylarylsulfonates (for example calcium dodecylbenzenesulfonate), alkylsulfates (for example sodium dodecylsulfate), sulfosuccinates (for example sodium dioctylsulfosuccinate), alkylethersulfates, alkylarylethersulfates, alkylether carboxylates, alkylarylethercarboxylates, lignin sulfonates or phosphate esters. Suitable non-ionic emulsifiers and surfactants include fatty acid ethoxylates, ester ethoxylates, glyceride ethoxylates (for example castor oil ethoxylate), alkylaryl polyglycol ethers (for example nonylphenol ethoxylates), alcohol ethoxylates, propylene oxide-ethylene oxide condensation products, amine ethoxylates, amide ethoxylates, amine oxides, alkyl polyglucosides, sorbitan fatty acid esters, polyoxyethylene sorbitan fatty acid esters, polyoxyethylenesorbitol esters or alcohol ethoxy carboxylates, especially those obtainable from $C_{12-14}$-alcohols.

A preferred formulation suitable for use in synthetic, semi-synthetic and soluble oil metal working fluids comprises:

(a) from 10 to 60, more preferably from 15 to 45 and especially from 18 to 25 parts of the compound of Formula (1); and (b) from 90 to 40, more preferably from 85 to 55 and especially from 82 to 75 parts of a water miscible solvent selected from a $C_{2-12}$-diol and a polyalkylene glycol containing up to 12 carbon atoms;

wherein the parts are by weight and the sum of the parts (a)+(b)=100.

Examples of preferred formulations include those in which the ratio of component (a) to component (b) is 40:60 and 20:80 by weight.

The compound of Formula (1) may be used in conjunction with one or more further antimicrobial compound(s) in the method according to the present invention. The addition of further antimicrobial compound(s) to the metal working fluid can provide a broader spectrum of antimicrobial activity than the compound of Formula (1) alone. Furthermore, the combination of the compound of Formula (1) and further antimicrobial compound(s) may provide a synergistic effect.

The further antimicrobial compound(s) may possess antibacterial, anti-fungal, anti-algal or other antimicrobial activity. Suitable further antimicrobial compounds which may be used include quaternary ammonium compounds, urea derivatives, antimicrobial amino compounds for example dodecylamine or 2-[(hydroxymethyl)-amino]ethanol; antimicrobial imidazole derivatives; antimicrobial nitrile compounds, for example 2-bromo-2-bromomethylglutaronitrile; antimicrobial thiocyanate derivatives, for example methylene(bis)thiocyanate; isothiazolin-3-ones, for example 5-chloro-2-methyl-4-isothiazolin-3-one, 2-methyl-4-isothiazolin-3-one, 4,5-dichloro-2-methylisothiazolin-3-one 2-n-octylisothiazolin-3-one, 4,5-trimethylene4-isothiazolin-3-one and 2-methyl-4,5-trimethylene-4-isothiazolin-3-one and mixtures thereof; thiazole derivatives, antimicrobial nitro compounds, iodine compounds, for example 3-iodo-2-propynyl-N-n-butyl carbamate; aldehydes and aldehyde release agents, for example glutaraldehyde (pentanedial), formaldehyde or glyoxal; amides for example chloracetamide, guanidine derivatives; antimicrobial thiones; antimicrobial triazine derivatives, for example hexahydro-1,3,5-tris(2-hydroxyethyl)triazine and hexahydro-1,3,5-triethyltriazine; oxazolidine and derivatives thereof, furan and derivatives thereof; antimicrobial carboxylic acids and the salts and esters thereof; phenol and derivatives thereof; salts and complexes of 2-pyridinethione-1-oxide, especially alkali metal salts, for example sodium pyridine-2-thiol-1oxide and the 2:1 zinc complex of 1-hydroxy-pyridine-2-thione; antimicrobial sulphone derivatives; imides; thioamides; azole fungicides and strobilurin fungicides.

The amount of further antimicrobial compound(s) used will depend upon the further antimicrobial compound and the metal working fluid to which the compound(s) are added.

Preferably the weight ratio of the further antimicrobial compound(s): total weight of the compound of Formula (1) is from 10:1 to 1:10, more preferably from 5:1 to 1:5 and especially from 2:1 to 1:2.

The further antimicrobial compound(s) and the compound of Formula (1) may be added to the metal working fluid in any order or simultaneously. When the further antimicrobial compound(s) and the compound of Formula (1) are added simultaneously they are preferably formulated together, optionally with a carrier. Suitable carriers are as hereinbefore defined with reference to the first aspect of the current invention, especially the hereinbefore described liquid carriers. When the carrier is a liquid, the formulation may comprise an emulsion, micro-emulsion, suspension or solution of the compound of Formula (1) and further antimicrobial compound(s) in the liquid carrier.

The compounds of Formula (1) are oily liquids at ambient temperatures. We have found that the compounds of Formula (1) are solvents for many organic anti-microbial compounds. This property can be utilised to form a solution of the further anti-microbial compound in the compound of Formula (1), thereby forming a liquid concentrate without the need for additional solvents. The liquid concentrate can then be conveniently added to the metal working fluid directly or can be further diluted for example using a solvent, or by emulsifying the concentrate in a liquid carrier with a suitable emulsifying agent.

In a preferred embodiment of the present invention the further antimicrobial compound is a salt of pyridine-2-thiol-1-oxide, such as a metal salt, especially a sodium or zinc salt and more preferably a sodium salt (for example that commercially available from Arch Chemicals under the trademark Sodium Omadine).

We have found that the use of a composition comprising a compound of Formula (1) and a salt of pyridine-2-thiol-1-oxide, especially the sodium salt, in the method according to the present provides a synergistic effect compared to the use of the two compounds alone, especially against fungi such as *Fusarium solani*. This composition exhibits a sum of the Fractional Inhibitory Concentration (hereinafter FIC) for each component which has a value less than 1. The FIC is the ratio of the amount of each component in the composition relative to its Minimum Inhibitory Concentration (MIC) when used alone. Thus, when the sum of the FIC values is one, the two components exhibit a mere additive effect. When the sum of the FIC values is below one, the mixture is synergistic. When the sum of the FIC values is between one and two the two components are considered to act independently. When the sum of the FIC values is greater than two, the mixture is antagonistic. The FIC values are preferably determined by constructing an isobologram wherein each component in a matrix array is varied stepwise from a concentration in excess of the MIC down to zero ppm. Therefore, an isobologram, allows the smallest value of the sum of the FIC's for each component in the composition to be determined and hence the optimal concentration for each component in the composition.

According to a second aspect of the present invention there is provided a composition comprising:

(a) a compound of Formula (1); and (b) a salt of pyridine-2-thiol-1-oxide.

The preferred compounds of Formula (1) in the composition according to the second aspect of the invention are the preferred compounds hereinbefore described in relation to the first aspect of the invention. It is especially preferred that the compound of Formula (1) is 2-n-butyl-1,2-benzisothiazolinone.

Preferably component (b) of the composition is the sodium or zinc salt of pyridine-2-thiol-1-oxide and most preferably the sodium salt.

The weight ratio of component (a):component (b) may vary over wide limits, for example from 1:99 to 99:1, such as from 10:1 to 1:10, and more preferably from 1:2 to 2:1. It especially preferred that the weight ratio of the two components is close to the ratio which gives the minimum value for the sum of the FIC values for each component of the composition. This ratio is readily determined from an isobologram as described above.

The compound of Formula (1) and the salt of pyridine-2-thiol-1-oxide may be added to the metal working fluid directly. However for ease of handling and dosing, it is generally convenient to formulate the composition according to the second aspect of the present invention with a suitable carrier.

The carrier may be a solid but is preferably a liquid medium and the formulation of the two components is preferably in the form of a solution, dispersion, emulsion or micro-emulsion in the liquid medium.

A suitable carrier for the two components is generally one which provides a sufficient solubilising effect for the two components in the metal working fluid and also one which is compatible with the metal working fluid to be protected: Suitable carriers are generally selected according to the metal working fluid to be protected. Examples of suitable carriers are those previously listed with reference to the first aspect of the present invention.

If the composition according to the second aspect of the invention is in the form of a suspension, emulsion or dispersion, it preferably also contains a surface active agent to produce a stable dispersion or to maintain the non-continuous phase uniformly distributed throughout the continuous phase. Suitable surface active agents are ones which do not have a significant adverse effect on the biocidal activity of the components (a) and (b). Suitable surface active agents include emulsifiers, surfactants and thickeners and mixtures thereof, and are described herein with respect to the first aspect of the current invention.

Preferably, the sum of the FIC values of the components in the composition is not greater than 0.8, more preferably not greater than 0.7 and especially not greater than 0.5.

The compositions according to the second aspect of the invention have been found to be particularly useful at inhibiting the growth of micro-organisms in metal working fluids. It will be readily appreciated that the composition may also be used to protect other media, especially industrial media and personal care formulations, which are susceptible to microbiological and especially fungal degradation. Examples of such industrial media are cooling tower liquors, geological drilling muds, hydraulic fluids, latices, paints, lacquers, adhesives, sealants, wood, leather, pigments and inks. Examples of personal care formulations include shampoos, cosmetics, fragrances and hand lotions. Generally, the amount of the composition according to the second aspect of the invention is from 1 to 250 ppm and preferably from 10 to 100 ppm of the composition relative to the medium.

According to a third aspect of the present invention there is provided a metal working fluid containing a compound of the Formula (1) as hereinbefore described in relation to the first aspect of the present invention.

The preferred metal working fluids and compounds of the Formula (1) for use in this aspect of the invention are as hereinbefore described in relation to the first aspect of the present invention.

The invention is further illustrated by the following examples in which all parts are by weight unless otherwise stated:

EXAMPLES 1 to 3

Temperature Stability of 2-n-butyl-benzisothiazolin-3-one in Synthetic Metal Working Fluids The biocides shown in Table 1 were added to Trim C111A (ex. Master Chemical Corporation, USA, a synthetic water miscible cutting and grinding fluid used as coolant and lubricant in metal removal processes). The initial concentration of the biocide in the metal working fluid is shown in the third column of Table 1. The metal working fluid was then stored at 50° C. for 45 days.

The concentration of biocide remaining after storage was measured using reverse phase high performance liquid chromatography (HPLC) after initial sample preparation. In the case of 2-n-butyl-benzisothiazolin-3-one, 2-n-octyl-isothiazolin-3-one and 3-iodo-2-propynyl-N-butylcarbamate sample preparation involved solvent extraction of the active from the metal working fluid. For sodium pyrithione, initial sample preparation was derivatisation to produce a compound readily detectable by HPLC. The concentration of each biocide remaining after storage at 50° C. is shown in the fourth column of Table 1.

TABLE 1

Stability in Synthetic Metal Working Fluid

| Example | Biocide | Initial concentration (ppm) | % Remaining after storage at 50° C. for 45 days |
|---|---|---|---|
| 1 | BBIT | 1500 | 23 |
| 2 | BBIT | 2000 | 38 |
| 3 | BBIT | 2500 | 40 |
| Comparative 1 | Sodium Omadine | 2500 | 0 |
| Comparative 2 | OIT | 2000 | 0 |
| Comparative 3 | IPBC | 5000 | 0 |

Footnote to Table 1:
BBIT is 2-n-butyl-1,2-benzisothiazolin-3-one, ex Avecia Ltd Sodium Omadine is a trademark name for sodium pyridine-2-thiol-1-oxide, ex. Arch Chemicals
OIT is 2-n-octyl-isothiazolin-3-one, ex Rohm & Haas
IPBC is 3-iodo-2-propynyl-N-n-butyl carbamate, ex Arch Chemicals Table 1 clearly shows that 2-n-butyl-1,2-benzisothiazolin-3-one is considerably more stable to high temperature storage than the biocides in the comparative examples. For example in Comparative Example 3, despite using twice the initial concentration of IPBC as the BBIT in Example 3, no IPBC remained after storage. On the-other hand 40% of the BBIT (i.e. a compound of Formula (1)) remained in the metal working fluid.

EXAMPLES 3 to 7

Temperature Stability of 2-n-butyl-benzisothiazolin-3-one in Semi-Synthetic and Soluble Oil Metal Working Fluids The stability of the biocides shown in Tables 2 and 3 in semi-synthetic and soluble oil metal working fluids was assessed using the same method described above in Example 1.

TABLE 2

Stability in Semi-Synthetic Metal Working Fluid (Quaker fluid No. 12717, ex Quaker Inc.)

| Example | Biocide | Initial concentration (ppm) | % Remaining after storage at 50° C. for 45 days |
|---|---|---|---|
| 3 | BBIT | 1500 | 33 |
| 4 | BBIT | 2000 | 40 |
| 5 | BBIT | 2500 | 46 |
| Comparative 4 | Sodium Omadine | 2500 | 0 |
| Comparative 5 | OIT | 2000 | 0 |
| Comparative 6 | IPBC | 5000 | 0 |

TABLE 3

Stability in Soluble Oil Metal working Fluid

| Example | Biocide | Initial concentration (ppm) | % Remaining after storage at 50° C. for 45 days |
|---|---|---|---|
| 5 | BBIT | 1000 | 80 |
| 6 | BBIT | 2000 | 78 |
| 7 | BBIT | 600 | 50 |
| Comparative 7 | IPBC | 5000 | 13 |
| Comparative 8 | Sodium Omadine | 2500 | 0 |

Footnotes to Tables 2 and 3. BBIT, OIT, IPBC and sodium Omadine are as defined in the foot note to Table 1.

Tables 2 and 3 show that 2-n-butyl-1,2-benzisothiazolin-3-one is significantly more stable than the comparative biocides.

EXAMPLE 8

Inhibition of Micro-Organisms in Metal Working Fluid Concentrates

The following microbial strains were studied:

| Organism | Strain Number |
|---|---|
| Bacteria | |
| Pseudomonas oleovorans | ATCC 8062 |
| Escherichia coli | ATCC 8739 |
| Proteus mirablis | ATCC 4675 |
| Citrobacter freundii | ex MWF |
| Pseudomonas stutzeri | ATCC17588 |
| Yeast and Fungi | |
| Fusarium solani | ATCC 58877/IMI 314228 |
| Penicillium sp. | ATCC 66782 |
| Acremonium strictum | ATCC 36111/IMI 321985 |
| Geotrichum candidum | IMI 321760 |

Method

The biocides shown in Tables 4, 5 and 6 were added to the metal working fluid shown in each table and assessed for microbial resistance by a method based on ASTM E686-91: Standard Test Method for Evaluation of Antimicrobial Agents in Aqueous Metal Working Fluids as described below.

The metal working fluids used in the assessment were the same as those used in Examples 1 to 7.

Inoculum

Bacteria and fungi were gradually acclimatised to the metal working fluid. The organisms were grown up in biocide free metal working fluid (containing 50% (v/v) minimal broth) with aeration at 25° C. until microbial count reached $10^9$ cfu/ml. Every 7 days each micro-organism was subcultured into 90 ml (10 ml inoculum) and re-incubated. Subculturing was done for a minimum of three cycles before use.

Microbiological Test Procedure

To 1l French square bottles, 900 ml of metal working fluid was added at use concentration (diluted to 5% with water of 125 ppm calcium hardness). 100 ml of inoculum was added and mixed (100 ml of total quantity was removed and discarded). The metal working fluid was allowed to sit undisturbed for 64 hours. The metal working fluid was mixed and sampled for microbiological testing.

Bacteria and fungi were enumerated by streaking an aliquot onto nutrient or malt agar as appropriate. The mixtures were aerated using capillary tubing to bubble air into the bottom of the bottle (introduced by means of a multi-valve air manifold). Antifoam was also added. After 5 days, the aeration was stopped and volume replaced with sterile distilled water. The mixture was allowed to sit for 64 hours and then mixed. 10 ml of inoculum was used to re-inoculate and all losses were replaced with Biocide containing metal working fluid. The pH of the metal working fluid was measured at start of test and every 7 days. The physical condition of the metal working fluid was noted at the start of the test and every 7 days. Aeration was resumed and the regime repeated for a minimum of 6 weeks or until failure.

Results

TABLE 4

Synthetic Metal Working Fluid

| Biocide | Conc. (a.i.) | Fungal Contamination after (days) | | | |
|---|---|---|---|---|---|
| | | 10 | 31 | 87 | 110 |
| Control | 0 ppm | +++ | +++ | +++ | +++ |
| Kathon 893W + Sodium omadine | 45 ppm + 50 ppm | – | + | + | ++ |
| BBIT | 75 ppm | – | – | – | – |
| BBIT | 100 ppm | – | – | – | – |
| BBIT | 150 ppm | – | – | – | – |
| Sodium omadine | 150 ppm | ++ | +++ | +++ | +++ |
| IPBC | 75 ppm | – | – | – | – |

TABLE 5

Semi Synthetic Metal Working Fluid

| | | Fungal Contamination after (days) | | | |
|---|---|---|---|---|---|
| | | 10 | 31 | 87 | 110 |
| Control | 0 ppm | – | + | + | ++ |
| Kathon 893W + Sodium omadine | 45 ppm + 50 ppm | – | – | – | + |
| BBIT | 75 ppm | – | – | + | + |
| BBIT | 100 ppm | – | – | – | – |
| BBIT | 150 ppm | – | – | – | – |
| Sodium omadine | 150 ppm | – | – | + | + |
| IPBC | 75 ppm | – | – | – | – |

TABLE 6

Soluble Oil Metal Working Fluid

| | | Fungal Contamination after (days) | | | |
|---|---|---|---|---|---|
| | | 10 | 31 | 87 | 110 |
| Control | 0 ppm | +++ | +++ | +++ | +++ |
| Vantropol T + Sodium omadine | 1140 ppm + 50 ppm | – | – | + | +++ |
| Vantropol T + IPBC | 1140 ppm + 45 ppm | – | – | – | – |
| Vantropol T + BBIT | 1140 ppm + 50 ppm | – | – | – | – |
| Vantropol T + BBIT | 1140 ppm + 30 ppm | – | – | – | – |
| Vantropol T + BBIT | 760 ppm + 50 ppm | – | – | – | + |
| Vantropol T + BBIT | 760 ppm + 100 ppm | – | – | – | – |

Footnotes to Tables 4, 5 and 6
BBIT is 2-n-N-butyl-1,2-benziosothiazolin-3-one, ex. Avecia Limited
Kathon 893 W is a trademark name for 2-n-octyl-4-isothiazolin-3-one, ex Rohm and Haas
Sodium Omadine is a trademark name for sodium pyridine-2-thiol-1-oxide, ex Arch Chemicals
IPBC is 3-iodo-2-propynyl-N-n-butyl carbamate, ex Arch Chemicals
Vantropol T is a trademark name for 1,3,5-tris(hydroxyethyl)-1,3,5-triazine, ex. Avecia Limited.
+++ indicates confluent growth
++ indicates moderate growth
+ indicates slight growth
– indicates no growth The data in Tables 4 to 6 shows that the method according to the present invention provides good protection -against the growth of fungi, yeasts and bacteria in metal working fluids.

EXAMPLE 9

Synergistic Compositions

The fungus *Fusarium solani* (ATCC 58877/IMI 314228) was grown in malt agar for 7–14 days at 25° C. to give a mycelial mat and the spores harvested from the surface using physiological saline to give a suspension containing about $10^6$ fungal spores/ml. This was then diluted with malt broth to give a spore suspension containing $10^4$ spores/ml. A 100 µl aliquot of this spore suspension was added to each well of a microtitre plate except for the first well which contained 180 µl.

2-n-butyl-1,2-benzisothiazolin-3-one (BBIT) was dissolved in dimethylformamide at a concentration of 0.25 mg/ml. A 20 µl aliquot of this solution was added to the first well of the microtitre plate and thoroughly mixed. 100 µl was withdrawn from the first well, added to the second well and mixed. This process was repeated along each row of the wells in the microtitre plate so that the concentration of the chemical under evaluation was progressively reduced by a doubling dilution technique. The growth of fungi was assessed by visual inspection after incubation for 5 days at 25° C. to determine the MIC value of BBIT against each of the fungi in Table 1. This procedure was repeated to determine the MIC of sodium pyridine-2-thiol-1-oxide (Sodium Omadine). The results are given in Table 7:

TABLE 7

| MIC values (ppm) | |
|---|---|
| BBIT | sodium pyridine-2-thiol-1-oxide |
| 6.4 | 18.5 | b) Determination of FIC Fractional Inhibitory Concentration

A matrix was constructed in a 10×10 array in microtitre wells wherein the concentration of each chemical was varied stepwise by serial dilution from a concentration of twice the MIC down to zero. As each microtitre plate contains only 96 wells the combination of the two compounds making up the extreme concentrations (highest and lowest) were omitted. Each mixture (100 µl) was added to the plate so that the total volume was maintained at 200 µl. By transferring 100 µl from each well to the adjacent well containing 100 µl nutrient the concentration of the chemical was reduced from twice the MIC to zero in a stepwise manner.

The presence or absence of growth was determined visually after incubation. The plates containing fungi were incubated for 40–72 hours at 25° C. From the matrix an isobologram was created and the FIC for each chemical of the composition calculated. The FIC is the ratio of the concentration of chemical which inhibits growth when applied as a combination of chemicals relative to the MIC for that chemical when applied alone.

FIC values for both compounds in the mixture were calculated and results are shown in Table 8. The sum of these two figures gives an indication of the action of the two biocides. A value less than one indicates a synergistic effect, if the total is unity or greater the action is additive and if the value is greater than two the biocides are antagonistic. If a graph is constructed with axes representing biocide Fractional Inhibitory concentrations on linear scales, when the combination is additive the isobole (i.e. the line joining the points that represent all combinations with the same effect including the equally effective concentrations of the Biocides used alone) is straight, synergistic combinations give concave isoboles and antagonistic combinations give convex isoboles

TABLE 8

| Biocide | FIC Value | | | | |
|---|---|---|---|---|---|
| BBIT | 0 | 0.33 | 0.33 | 0.67 | 1 |
| Sodium Omadine | 1 | 0.29 | 0.15 | 0.15 | 0 |
| Sum of FIC Values | 1 | 0.62 | 0.48 | 0.82 | 1 |

Table 8 clearly shows synergy between BBIT and Sodium Omadine against *Fusarium solani*.

Graph 1 is an isobologram Illustrating the synergistic effect encountered using a BBIT and sodium omadine composition in a metal working fluid as specified by the results in table 8.

Graph 1

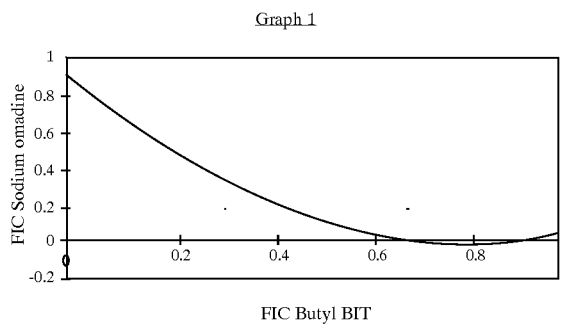

Foot notes to Tables 7 and 8 and Graph 1

Sodium omadine is a trademark name for sodium pyridine-2-thiol-1-oxide, ex Arch Chemicals.

BBIT represents 2-n-N-butyl-1,2-benzoisothiazoline-3-one ex. Avecia Limited.

What is claimed is:

1. A formulation suitable for use in synthetic, semi-synthetic and soluble oil metal working fluids comprising:

(a) from 10 to 60 parts of the compound of Formula (1)

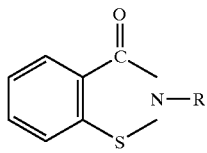

Formula (1)

wherein:

R is $C_{4-5}$-alkyl; and (b) from 90 to 40 parts of a water miscible solvent selected from a $C_2$–$C_{12}$ diol and a polyalkylene glycol containing up to 12 carbon atoms;
wherein the parts (a) and (b) are by weight and the sum of the parts of (a) and (b)=100.

2. A formulation according to claim 1 wherein the compound of Formula 1 is 2-n-butyl-1,2-benzisothiazolinone.

3. A formulation according to claim 1 or 2 wherein the water miscible solvent is diethylene glycol or dipropylene glycol.

4. A composition comprising:

(a) a compound of Formula (1)

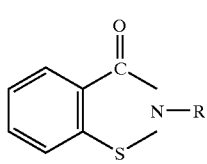

Formula (1)

wherein:

R is $C_{4-5}$-alkyl; and (b) a salt of pyridine-2-thiol-1-oxide, said composition demonstrating a synergistic fungicidal effect compared to component (a) or (b) alone.

5. A composition according to claim 4 wherein the compound of Formula (1) is 2-n-butyl-1,2,benzisothiazolinone.

6. A composition according to claim 5 wherein component (b) is sodium pyridine-2-thiol-1-oxide.

7. A composition according to claim 4 or 5 wherein component (b) comprises sodium or zinc pyridine-2-thiol-1-oxide.

8. A composition according to claim 4 or claim 5 wherein the weight ratio of component (a) to component (b) is 1:99 to 99:1.

9. A composition according to claim 8 wherein said weight ratio is from 10:1 to 1:10.

10. A composition according to claim 8 wherein the weight ratio of component (a) to component (b) is from 1:2 to 2:1.

11. A composition according to claim 4 or claim 5 which further comprises a carriers.

12. A composition according to claim 11 which comprises:

(a) from 10 to 60 parts of a mixture of the compound of Formula (1) and a salt of pyridine-2-thiol-1-oxide; and (b) from 40 to 60 parts of a carrier;
wherein the parts (a) and (b) are by weight and the sum of the parts (a) and (b) 100.

13. A composition according to claim 11 wherein the carrier comprises a mixture of water and a water miscible organic solvent selected from a $C_{2-12}$ diol and a polyalkylene glycol containing up to 12 carbon atoms.

14. A composition according to claim 13 wherein the carrier comprises a mixture of water and diethylene glycol and/or dipropylene glycol.

15. A metal working fluid containing a compound of the Formula (1):

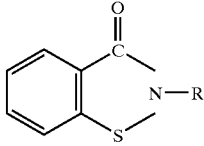

Formula (1)

wherein:

R is $C_{4-5}$-alkyl.

16. A method for inhibiting the growth of microorganisms in a metal working fluid comprising adding to the metal working fluid a benzisothiazolin-3-one of the Formula (1):

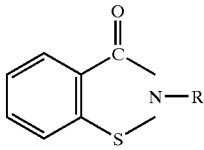

Formula (1)

wherein:

R is $C_{4-5}$-alkyl.

17. A method according to claim 16 wherein R is n-butyl.

18. A method according to claim 17 which comprises also adding sodium pyridine-2-thiol-1-oxide to the metal working fluid to obtain a synergistic fungicidal effect.

19. A method according to claim 16 wherein the metal working fluid is a straight oil, a soluble oil, a semi-synthetic metal working fluid.

20. A method according to claim 16 wherein the compound of Formula (1) is added to a concentrate or pre-mix of the metal working fluid.

21. A method according to claim 16 wherein the compound of Formula (1) is present in the metal working fluid in a concentration of from 50 ppm to 300 ppm by weight.

22. A method according to claim 21 wherein the compound of Formula (1) is present in the metal working fluid in a concentration of from 100 ppm to 150 ppm by weight.

23. A method according to claim 16 which further comprises the addition of one or more further antimicrobial compound(s) to the metal working fluid.

24. A method according to claim 23 wherein the weight ratio of the further antimicrobial compound(s) to the compound of Formula (1) added to the metal working fluid is from 10:1 to 1:10.

25. A method according to claim 24 wherein said weight ratio is from 2:1 to 1:2.

26. A method according to claim 23 or claim 24 wherein the further antimicrobial compound comprises a salt of pyridine-2-thiol-1-oxide.

27. A method according to claim 26 wherein said salt is sodium pyridine-2-thiol-1-oxide.

28. A method according to claim 23 or claim 24 wherein the compound of Formula (1) and/or the further antimicrobial compound(s) are added to the metal working fluid in formation with a carrier.

* * * * *